United States Patent [19]

Henley

[11] Patent Number: 5,432,461
[45] Date of Patent: Jul. 11, 1995

[54] METHOD OF TESTING ACTIVE MATRIX LIQUID CRYSTAL DISPLAY SUBSTRATES

[75] Inventor: Francois J. Henley, Los Gatos, Calif.

[73] Assignee: Photon Dynamics, Inc., San Jose, Calif.

[21] Appl. No.: 722,963

[22] Filed: Jun. 28, 1991

[51] Int. Cl.⁶ .................... G01R 31/302; G01R 31/02
[52] U.S. Cl. .................................. 324/770; 345/87; 345/904; 348/129
[58] Field of Search .................. 324/158 R, 96, 770; 345/87, 904; 348/129

[56] References Cited

U.S. PATENT DOCUMENTS

| | | | |
|---|---|---|---|
| 3,992,663 | 11/1976 | Seddick | 324/52 |
| 4,242,635 | 12/1980 | Burns | 324/158 |
| 4,355,278 | 10/1982 | Burns et al. | 324/158 |
| 4,368,523 | 1/1983 | Kawate | 365/63 |
| 4,444,801 | 4/1984 | Hongo et al. | 427/10 |
| 4,463,073 | 7/1984 | Miyauchi et al. | 430/5 |
| 4,465,969 | 8/1984 | Tada et al. | 324/96 |
| 4,507,605 | 3/1985 | Geisel | 324/73 |
| 4,510,222 | 4/1985 | Okunaka et al. | 430/5 |
| 4,523,847 | 6/1985 | Bjorklund et al. | 356/349 |
| 4,542,333 | 9/1985 | Koontz | 324/52 |
| 4,563,093 | 1/1986 | Tada et al. | 356/368 |
| 4,618,819 | 10/1986 | Mourou et al. | 324/77 |
| 4,631,576 | 12/1986 | St. John | 358/65 |
| 4,633,242 | 12/1986 | Sekiya | 340/719 |
| 4,636,403 | 1/1987 | Fisanick et al. | 427/53 |
| 4,688,900 | 8/1987 | Doane et al. | 350/347 |
| 4,727,234 | 2/1988 | Oprysko et al. | 219/121 |
| 4,758,092 | 7/1988 | Heinrich et al. | 356/36 |
| 4,776,022 | 10/1988 | Fox et al. | 382/8 |
| 4,819,038 | 4/1989 | Alt | 357/4 |
| 4,825,201 | 8/1989 | Watanabe et al. | 340/717 |
| 4,855,591 | 8/1989 | Nakamura et al. | 250/225 |
| 4,862,075 | 8/1989 | Choi et al. | 324/158 |
| 4,868,492 | 11/1989 | Beha et al. | 324/73 |
| 4,875,006 | 10/1989 | Henley et al. | 324/158 |
| 4,899,105 | 2/1990 | Akiyama | 324/158 |
| 4,906,922 | 6/1990 | Takahashi et al. | 324/158 |
| 4,910,458 | 3/1990 | Forsyth et al. | 324/158 |
| 4,944,576 | 7/1990 | Lacker et al. | 350/334 |
| 4,983,911 | 1/1991 | Henley | 324/158 |
| 4,999,577 | 3/1991 | Beha et al. | 324/158 |
| 5,017,755 | 5/1991 | Yahagi et al. | 219/121 |
| 5,037,683 | 7/1991 | Takahashi et al. | 324/158 |
| 5,043,297 | 8/1991 | Suzuki et al. | 437/51 |

FOREIGN PATENT DOCUMENTS

| | | |
|---|---|---|
| 3111393A1 | 9/1982 | Germany . |
| 56-153262 | 11/1981 | Japan . |
| 56-154678 | 11/1981 | Japan . |

OTHER PUBLICATIONS

System Tests Devices at GHz Rates, Lyle H. McCarty, Design News, Apr. 10, 1989.
Electro-Optic Device Tester Tops 1 GHz, John Novellino, Electronic Design, Sep. 8, 1988.
An Ultra High Speed Test System, Francois J. Henley, IEEE Design & Test of Computers, Feb. 1989.
** Electro-Optic Technology Supports Gigahertz
(List continued on next page.)

Primary Examiner—Ernest F. Karlsen
Attorney, Agent, or Firm—Townsend and Townsend Khourie and Crew

[57] ABSTRACT

A testing method for active matrix liquid crystal display substrates having thin film transistors provided with a plurality of pixel electrodes, a plurality of source lines, and a plurality of gate lines formed on a substrate. A high resolution electro-optical element whose optical properties change when an electrical field is impressed on it is disposed above the active matrix liquid crystal display substrate and separated therefrom by an extremely small gap. Electric current is caused to flow between the pixel electrodes on the active matrix liquid crystal display substrate and the transparent thin film electrodes on the surface of the electro-optical element, creating an electrical field in the electro-optical element. By detecting local changes in the optical properties of the electro-optical element, defects in the pixels of the active matrix liquid crystal display substrate can be detected.

7 Claims, 15 Drawing Sheets

OTHER PUBLICATIONS

Speeds; Francois J. Henley, Electronics Test, Sep. 1988.
** Using Electro-Optic Sampling Technology for Accurate Gigahertz ATE: Overview of the Art, Francois J. Henley, 1990 IEEE VLSI Test Symposium.
High Speed Pattern Generator and GaAs Pin Electronics For A Gigahertz Production Test System, D. J. Kratzer, S. Barton, F. J. Henley D. A. Plomgrem, Proceedings of IEEE 1988 Int'l Test Conf., Sep. 1988.
Test Head Using Electro-Optic Receivers and GaAs Pin Eloectronics for a Gigahertz Production Test System, F. J. Henley, H. J. Choi, Proceedings of IEEE 1988 Int'l Test Conference, Sep. 1988.
Achieving ATE Accuracy At Gigahertz Test Rates: Comparison of Electronic and Electro-Optic Sampling Technologies, F. J. Henley, H. J. Choi, Int'l Test Conf. Aug., 1989.
Systems Solutions Based on Electro-Optic Sampling to High Speed IC Test Problems, F. J. Henley, D. B. MacDonald, SPIE vol. 795 Characterization of Very High Speed Semiconductor Devices & Integrated Circuits (1987) pp. 345-351.
Characterization of High Speed (Above 500 MHz) Devices Using Advanced ATE-Techniques, Results and Device Problems, S. Barton, Proceedings of the IEEE 1989, Int'l Test Conf., Aug. 1989.
Testing and Qualifications of A-Si TFT-LC Color Cells for Military Avionics Applications; F. C. Luo et al.; SID 90 Digest; pp. 194-196.
Hitachi LCD Advertisement; pp. 2 and 3.
Measurement of Electro-Optic Characteristics of LCDs; M. E. Becker et al.; SID 90 Digest; pp. 163-166.
Testing and Qualificastions of a Si TFT-LC Color Cells for Military Avionics Applications; F. C. Luo et al.; SID 90 Digest; pp. 194-196.
In-Process Testing of Thin Film Transistor Arrays; R. Wisnieff et al.; SID 90 Digest pp. 190-193.
NCAP Displays: Optical Switching and Dielectric Properties; L. Welsh et al.; SID 90 Digest; pp. 220-223.

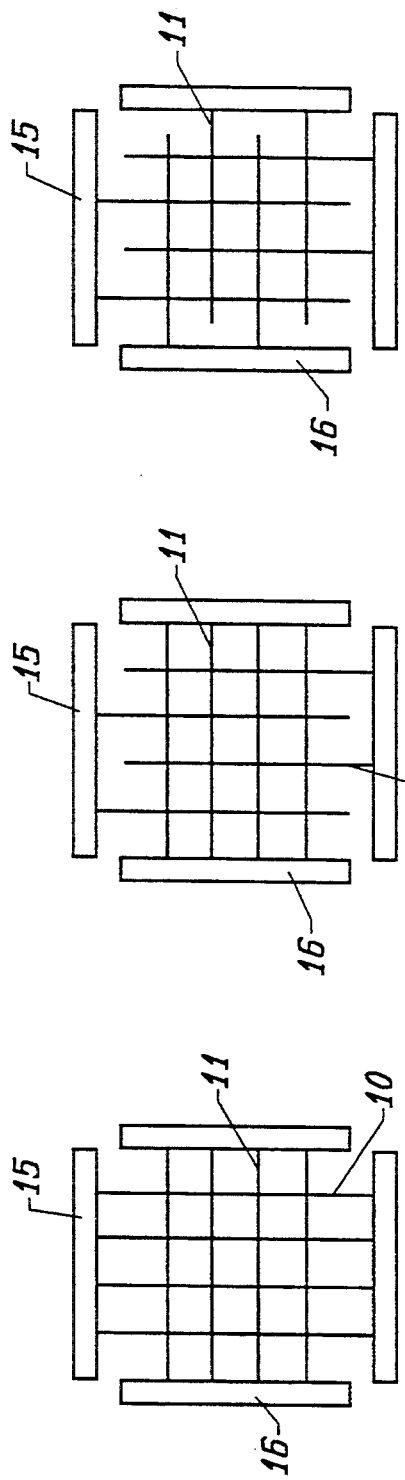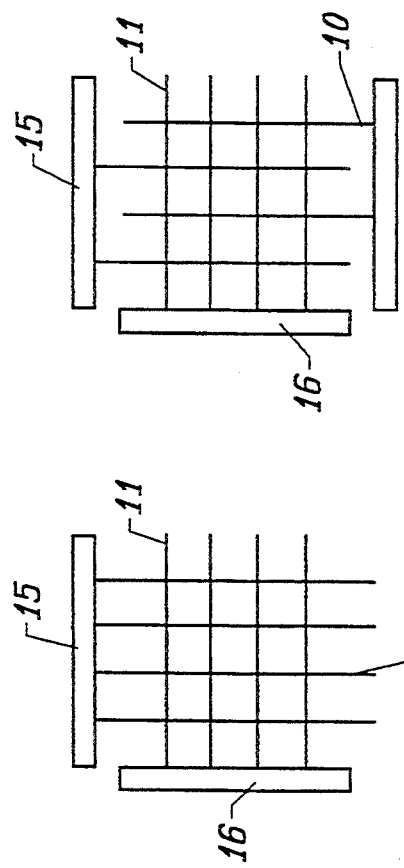

METHOD OF TESTING ACTIVE MATRIX LIQUID CRYSTAL DISPLAY SUBSTRATES

FIELD OF THE INVENTION

This invention relates to a testing method for the detection of defects produced in active matrix liquid crystal display substrates used as liquid crystal display panels, or the like.

BACKGROUND OF THE INVENTION

Active-matrix type liquid crystal display panels are formed using active-matrix liquid crystal display substrates which comprise pixel electrodes for each pixel element, arranged in a matrix pattern, gate lines which are common to all pixel electrodes, source lines, and thin film transistors. Generally, in this type of liquid crystal display panel, after the manufacture of an active matrix liquid crystal display substrate, by a transparent substrate, or the like, is disposed above the active matrix liquid crystal display substrate separated by a spacer, and the gap formed between the active matrix liquid crystal display substrate and the transparent substrate is filled with liquid crystal.

In liquid crystal televisions which are presently produced using this technique, there are many units which reach a pixel count of 250,000–500,000. Some have reached the market having a pixel count of over 1,000,000.

Formation of the pixels, and the numerous lines thereto corresponding, on a substrate, involve various formation processes which are carried out in a clean room. The clean room is controlled so that there is very little dust contained therein. However, when the pixels or the line width is extremely small, the presence of a small amount of microdust in the manufacturing atmosphere is directly linked to open-circuit or short-circuit defects of the pixel electrodes, gate lines or source lines. Presently, up to ten such defects are permitted. It is common to classify products as defective if the number of defects exceeds ten.

With present manufacturing technology, it is extremely difficult to reduce the number of such defects below the permitted limit, so that especially in liquid crystal display panels having a large number of pixels, the rate of defective products is startlingly high.

Present testing uses a probe to test active matrix liquid crystal display substrates when manufacturing is completed. When the number of elements on the active matrix liquid crystal display substrate is very large, an excessive amount of time is required for testing, and this approach becomes impractical.

Because of this, when liquid crystal display panels using active matrix liquid crystal display substrates are manufactured, testing was not carried out on the production line of the active matrix liquid crystal display substrates. After the completion of manufacturing, electrical power was applied to the liquid crystal display panel, and it was determined by eye whether each pixel was actuated or not. Even if defects were detected at this point, they were difficult to repair, and liquid crystal display panels were rejected and disposed of. This was a large cause of the extremely poor yield of active matrix liquid crystal displays.

SUMMARY OF THE INVENTION

It is an object of the present invention to provide a testing method in which defects in active matrix liquid crystal display substrates can be reliably and quickly discovered before assembly into liquid crystal panels, and the number and type of defects easily determined.

The present invention provides a testing method for active-matrix liquid crystal display substrates having thin film transistors, a plurality of pixel electrodes, source lines, and gate lines formed on a substrate. A high resolution electro-optical element in which the optical properties change when an electrical field is impressed across it, is placed above the active matrix liquid crystal display substrate and separated therefrom by an extremely small gap. A voltage is applied between the pixel electrodes on the active matrix liquid crystal display substrate and a transparent thin film electrode on the surface of the electro-optical element creating an electrical field across the electro-optical element. By detecting changes in the optical properties of the electro-optical element, the presence of defects in the pixels of an active matrix liquid crystal display substrate can be detected.

The present invention uses polymer-dispersed liquid crystals as the electro-optical element and detects defects in the pixels by detecting changes in the light transmission rate of the polymer-dispersed liquid crystals.

The present invention may also use Pockels crystals as the electro-optical element and detects defects in the pixels by detecting changes in the amount of polarization of reflected light.

The present invention irradiates the electro-optical element with light and receives the light reflected from the electro-optical element in a light detector, converts the amount of change in the reflected light to a corresponding voltage, and thus discerns the presence of defects in the pixels.

When an electric field is impressed on the electro-optical element, its optical properties change. When this electro-optical element is placed above the active matrix liquid crystal display substrate and an electric voltage applied between the pixel electrodes on the active matrix liquid crystal display substrate and transparent thin film electrodes on the electro-optical device, the optical properties of the electro-optical element change based on the magnitude of the electric field generated by each pixel electrode.

When an open circuit occurs in the pixel electrodes, gate lines, source lines, or other parts on the active matrix liquid crystal display substrate, some of the pixel electrodes do not operate. This causes the optical properties of the electro-optical elements above these pixel electrodes not to change. When there are short circuit defects, current flows to either the source lines or the gate lines, and abnormal phenomena, not present in normal pixels, occur. By detecting optical changes in the electro-optical element, it is possible to detect defects in the active matrix liquid crystal display substrate.

It is possible to use a polymer-dispersed liquid crystal, or a Pockels crystal, or the like, as the electro-optical element. The polymer-dispersed liquid crystal has an area in which the amount of light scattered is linearly proportional to the change in voltage. It is possible to take advantage of this linearity, and to relate the change in voltage as the change in the amount of light transmitted. It is preferable to apply a bias voltage up to this linear area.

The qualities of polymer-dispersed liquid crystals are especially suited to testing active matrix liquid crystal display substrates having extremely small lines or pixel electrodes. It is preferable to affix mylar, or the like, to the surface opposing the substrate of the polymer-dispersed liquid crystal as an insulating material so that the pixels on the active matrix liquid crystal display substrate are not destroyed.

By irradiating the electro-optical element with light, receiving the reflected light in a light detector, and converting the amount of change in the reflected light to a corresponding voltage, it is possible to express defects in the pixel electrodes of the active matrix liquid crystal display substrate as a change in the corresponding voltage.

BRIEF DESCRIPTION OF THE DRAWINGS

FIGS. 2(b)-(f) are top views showing examples of shorting bars;

DESCRIPTION OF AN EXEMPLARY PREFERRED EMBODIMENT

Figure 1:
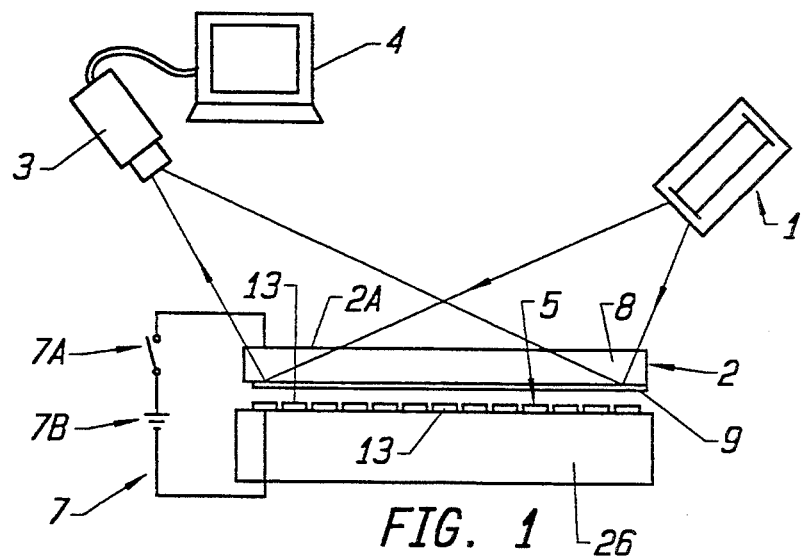
FIG. 1 is a block diagram showing an outline of the main parts of a test apparatus which is used in one embodiment of the present invention.

As shown in FIG. 1, the test apparatus is provided with a light source 1, and an electro-optical element 2 onto which the detection light is radiated by light source 1. A light detector 3 receives light reflected from the electro-optical element 2. A monitor 4 is connected to the light detector 3. An active matrix liquid crystal display substrate 5 is disposed facing, and slightly spaced apart from the opposing surface of electro-optical element 2. Reference number 7 indicates a voltage source which applies a fixed voltage between transparent thin film electrode 2a on the upper surface of electro-optical element 2 and active matrix liquid crystal display substrate 5. The voltage source is able to apply pulsed voltages separately to the source lines and gate lines, and can change the pulse voltage, pulse width, and period. Further details will be given hereinafter.

Light source 1 is a halogen lamp in one preferred embodiment. It is possible to use any type of laser light in place of the halogen lamp as light source 1.

The electro-optical element 2 is a polymer dispersed liquid crystal or Pockels crystal, or the like, the optical properties of which change when an electrical field is applied across it. The electro-optical element 2 shown in FIG. 1 is a sheet form polymer dispersed liquid crystal in which a reflecting body 9, such as non-conductive reflecting film or the like formed on the bottom surface of liquid crystal sheet 8, and transparent thin film electrode 2a are attached to the upper surface of liquid crystal sheet 8.

Liquid crystal sheet 8 is filled with NCAP (Nematic Curvilinear Aligned Phase) material which has a transmission rate which changes according to the magnitude of the electrical field created across liquid crystal sheet 8. The liquid crystal which fills the interior of liquid crystal sheet 8 is of a form in which a drop-shaped liquid crystal is dispersed in a high molecular weight substance, such as a polymer. The size of the ball-shaped droplets of the polymer which contains the resulting liquid crystal are controlled, and based on the magnitude of the electric field, a transparent state or a non-transparent state is caused to appear based on the agreement or disagreement of the index of refraction of the polymer and the liquid crystal. It is possible to use a Pockels crystal in which the amount of polarization of the reflected light changes based on the magnitude of the electric field applied. If the electro-optical element 2 used in the present preferred embodiment has optical properties which change when an electric field is impressed across it, such as the transmission rate of light or the amount of polarization of the reflected light, then electro-optical element 2 is not limited to the above, but any such element may be used.

A CCD camera or the like is used as light detector 3.

The active matrix liquid crystal display substrate 5 which is tested by the present method is commonly known and is used in liquid crystal display panels. As shown in FIG. 2, a number of source lines for the transmission of data signals, and a number of gate lines for the transmission of scanning signals, are formed on a substrate 12. Pixel electrodes 13 are formed between the source lines and gate lines. Each pixel electrode 13 is connected to source lines 10 and gate lines 11 through switching elements (thin film transistors) 14.

The line construction, pixel electrode construction, and the switching element construction of active matrix liquid crystal display substrate 5 are all known. It is possible to test these types of constructions with the method of the present invention.

Figure 2A:
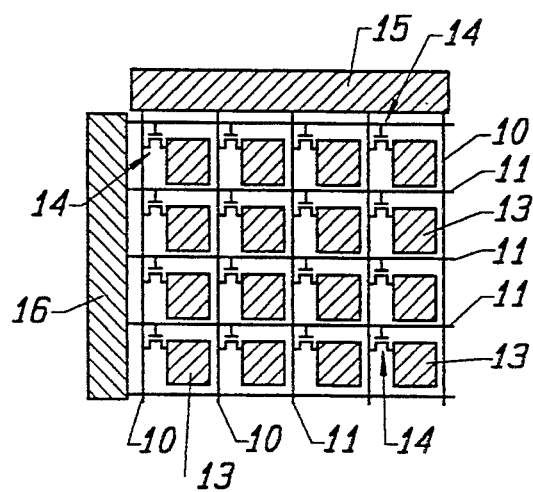
FIG. 2(a) is a partially expanded view of the active matrix liquid crystal display substrate tested by the present invention.

Reference number 15 shown in FIG. 2(a) indicates a shorting bar connecting source lines 10 and reference number 16 indicates a shorting bar connecting gate lines 11. Shorting bars 15 and 16 are formed in the manufacturing process of active matrix liquid crystal display substrate 5. They are cut and removed manufacturing the liquid crystal display panel.

Shorting bars 15 and 16 prevent static electricity from causing deleterious effects on the thin film transistors, and assist in the present testing method, (if they are in one of the forms shown in FIGS. 2(b)-2(f)). If mounted drivers are used in place of the shorting bars, the testing method of the present invention can still be used. Detection of line defects on the source and gate lines in FIG.

2(b), as well as line defects on the source lines in FIG. 2(c), has been thought to be difficult without optical techniques. However, at the substrate stage, even point defects which have been difficult to detect, can be detected using the present invention.

Voltage source 7 is provided with a switch 7a. A voltage source part 7b is connected to the transparent thin film electrode 2a on the upper surface of electro-optical element 2, and to the shorting bars 15 and 16 on active matrix liquid crystal display substrate 5, and is able to apply voltage from the gate lines and the source lines on all pixel electrodes 13 on active matrix liquid crystal display substrate 5. The voltage source 7 is able to apply pulsed voltages separately on source lines 10 and gate lines 11 and is able to freely change the pulse voltage, pulse width, and period.

Figure 2G:
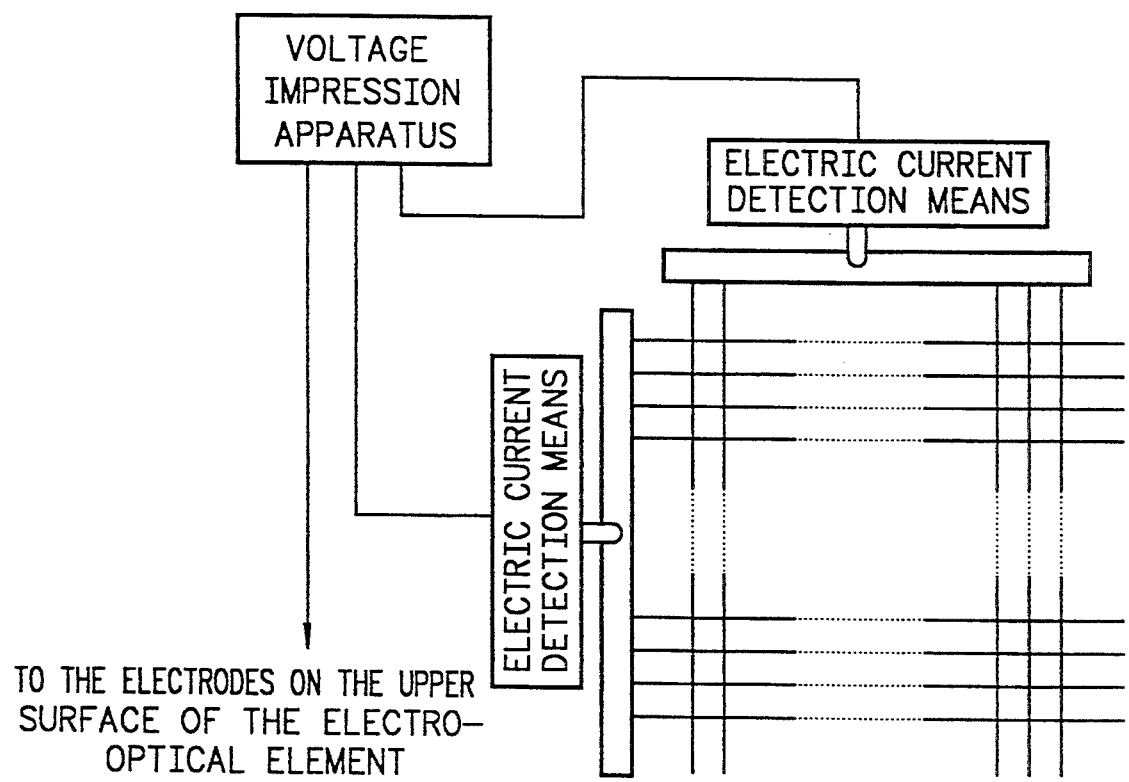
FIG. 2(g) is a block diagram showing a voltage source apparatus.

The construction of the connection of the voltage source 7 is shown in FIG. 2(g). When a shorting bar is formed like that shown in FIG. 2(g), a voltage pulse within the range of ±15 V from voltage source 7, makes contact with shorting bars 15 and 16 from two separate, independent terminals which are capable of current detection on the gate and source lines. Wiring is provided to transparent thin film electrode 2a on the upper surface of the electro-optical element from one terminal which is able to apply a fixed voltage with respect to the two terminals connected to shorting bars 15 and 16.

Figure 3:
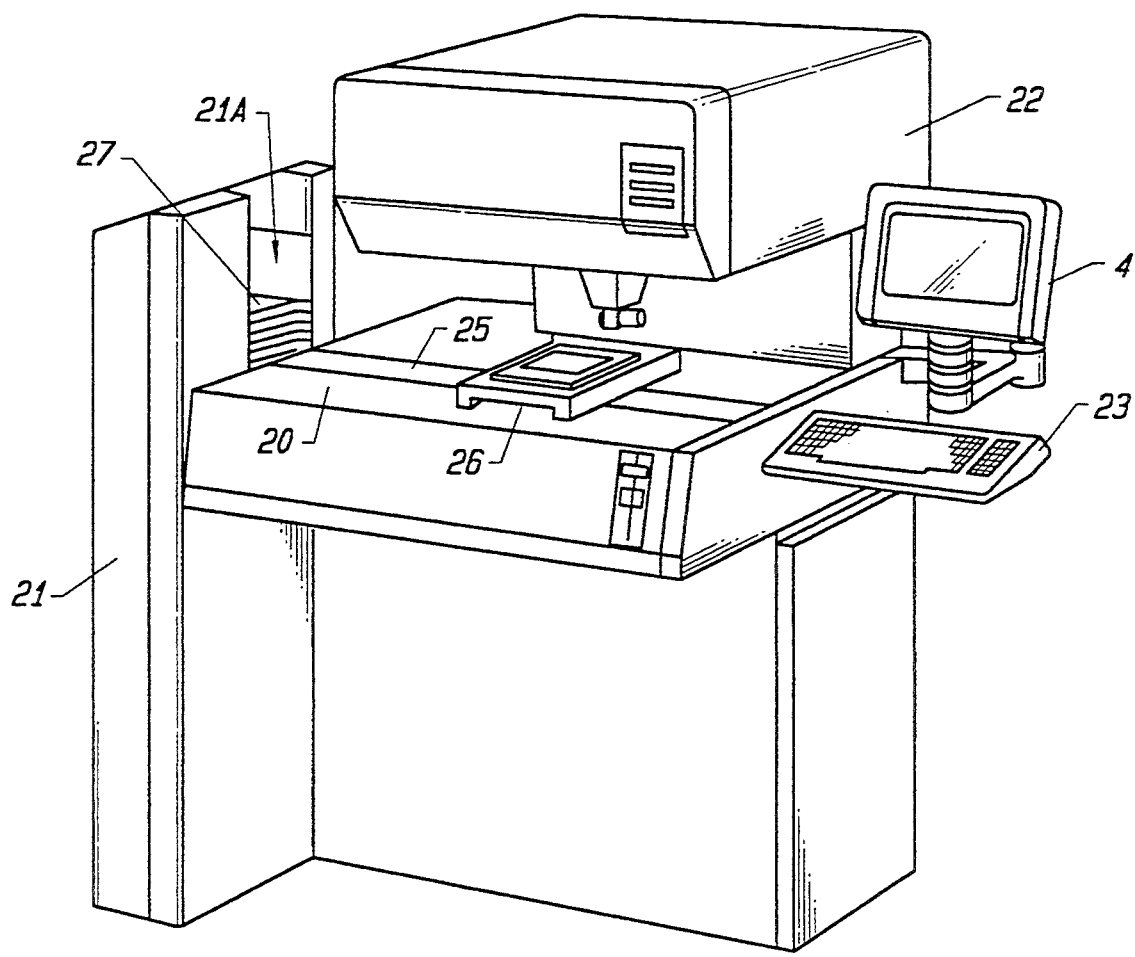
FIG. 3 is a block diagram showing the testing apparatus.

In FIG. 3, reference number 20 indicates a test bed. Reference number 21 indicates a substrate storage part (cassette rack) disposed at the left side of test bed 20. Reference number 22 indicates a test head, and reference number 23 indicates an operation board.

On the upper surface of test bed 20, in the central part thereof, a left to right guide rail 25 is laid. Table 26 runs along this guide rail 25 in the left and right directions. Mechanisms are installed on the bottom part of table 26 which move table 26 at right angles with respect to guide rail 25 so that table 26 is able to move in left, right, forward, and backward directions (that is, in the directions X and Y) above test bed 20 in a horizontal plane.

In the inner part of substrate storage part 21, a cassette 27 (see FIG. 7), stores a plurality of active matrix liquid crystal display substrates 5. Active matrix liquid crystal display substrates 5 are successively retrieved from the open mouth part of cassette 27 from the upper part of this substrate storage part 21 and are set on top of table 26.

Figure 4:
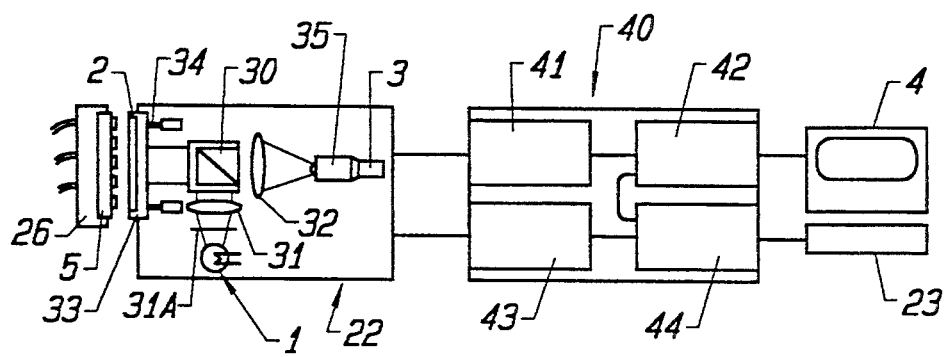
FIG. 4 is a block diagram of the interior test head of the testing apparatus.
Figure 5:
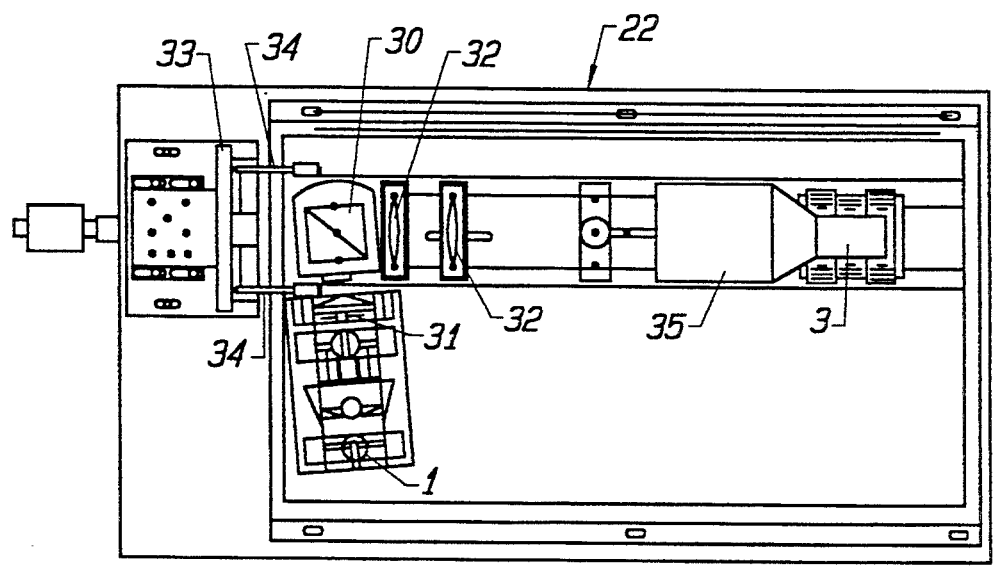
FIG. 5 is a more detailed drawing of the test head.

An outline of the composition of the inner part of test head 22 is shown in FIG. 4 and detailed construction of the inner part is shown in FIG. 5.

Here, the layout of each optical device in FIG. 5 can be freely changed by changing the setting position of the liquid crystal panel or the direction. In order to simplify the explanation, an example is shown in FIG. 4 and FIG. 5 in which the panel has been arranged lengthwise.

Light source 1 and light detector 3 are provided in the inner part of testing head 22. Light source 1 and light detector 3 each face a beam splitter 30. A lens 31 and a filter 31a provide adjustment between the beam splitter 30 and light source 1. A lens 32 provides for adjustment between beam splitter 30 and light detector 3. A holder 33 on which electro-optical element 2 is mounted is located on the left side of beam splitter 30 in FIG. 4. This holder 33 is capable of parallel movement in the left and right directions of FIG. 4 and FIG. 5 along support axles 34. A zoom lens 35 is mounted at the forward part of light detector 3, making possible the highly efficient entry of flight reflected from electro-optical element 2 into light detector 3.

Light emitted from light source 1 is irradiated onto electro-optical element 2 through beam splitter 30. After being reflected from the light reflection body 9 of electro-optical element 2, the light passes back through beam splitter 30, lens 32 and zoom lens 35 and into light detector 3.

In FIG. 4, reference number 40 indicates a controller. In this control part 40, is an analog-to-digital (A/D) converter 41 which is electrically connected to light detector 3, an image processor 42, a drive circuit 43, and a CPU 44. A display 4 is connected to image processor 42. Operation board 23 is connected to CPU 44.

Controller 40 converts the intensity of the light received by light detector 3 to a corresponding voltage and displays this strength. Controller 40 also displays the number of defects in the active matrix liquid crystal display substrate 5 and their positions and types in monitor 4 in response to the corresponding voltage distribution. When the number of defects is displayed, the dimensions of each pixel are inputted, and masking is conducted based on the corresponding voltage distribution.

Figure 6:
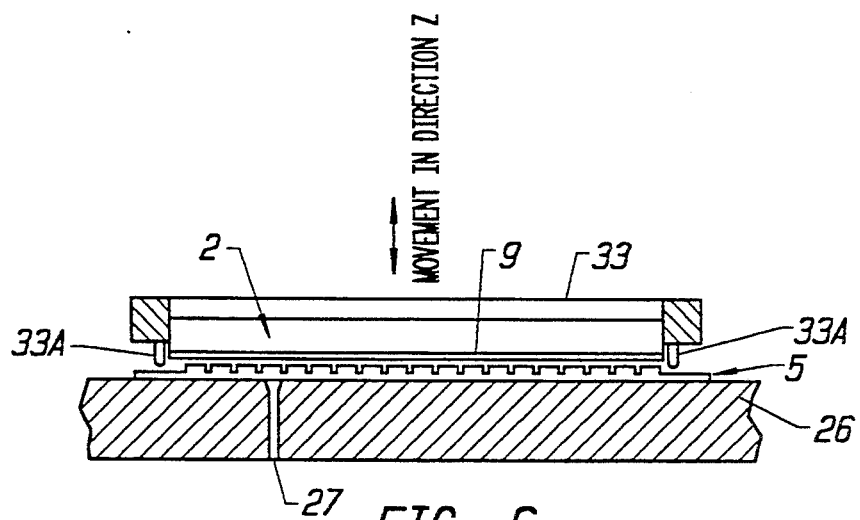
FIG. 6 is a side view showing the positioning of the holder used in the test apparatus and the active matrix liquid crystal display substrate.

Referring to FIG. 6, a passage 27 for air or vacuum, communicates the upper and lower sides of table 26, and is formed in table 26. A flexible pipe (not shown) is connected to the lower opening of passage 27 in such a way as not to obstruct the movement of table 26. This flexible pipe is connected to a vacuum. In this manner, an active matrix liquid crystal display substrate 5 is held on the upper surface of table 26 by vacuum adhesion through passage 27.

Figure 9:
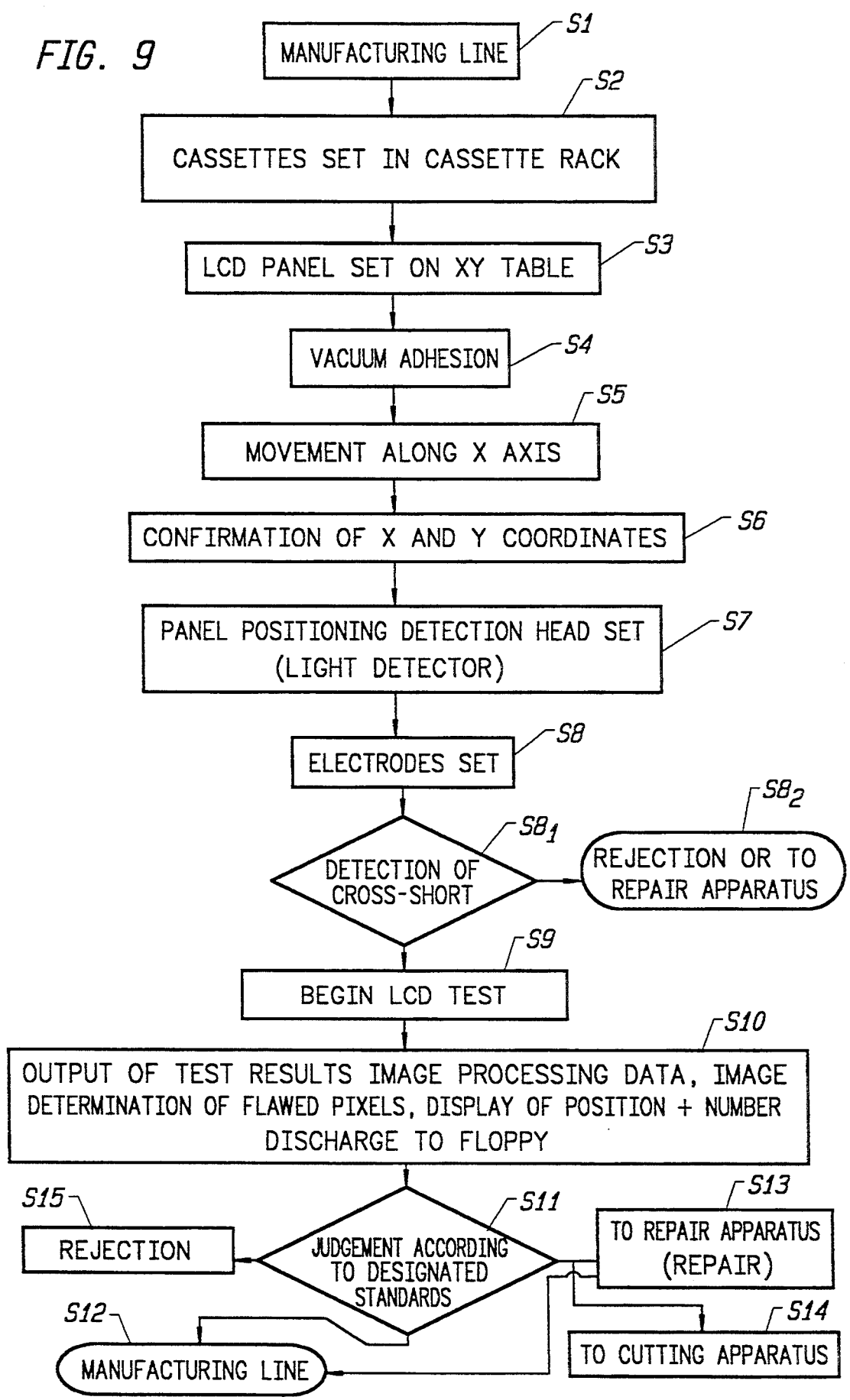
FIG. 9 is a flow chart illustrating test flow.

Testing of an active matrix liquid crystal display substrate 5 shown in FIG. 2 using a test apparatus constructed in accordance with the present invention, will be explained with reference to the flow chart of FIG. 9.

On a production line, active matrix liquid crystal display substrates 5 are manufactured by the formation of source lines 10, gate lines 11, pixel electrodes 13, switching elements 14, shorting bar 15, and shorting bar 16 on a substrate 12 by mask formation, thin film formation, photo resist, exposing the photo resist, etching, washing, ion impregnation, or similar various processes. This production line is shown as step S1 in FIG. 9.

Figure 7:
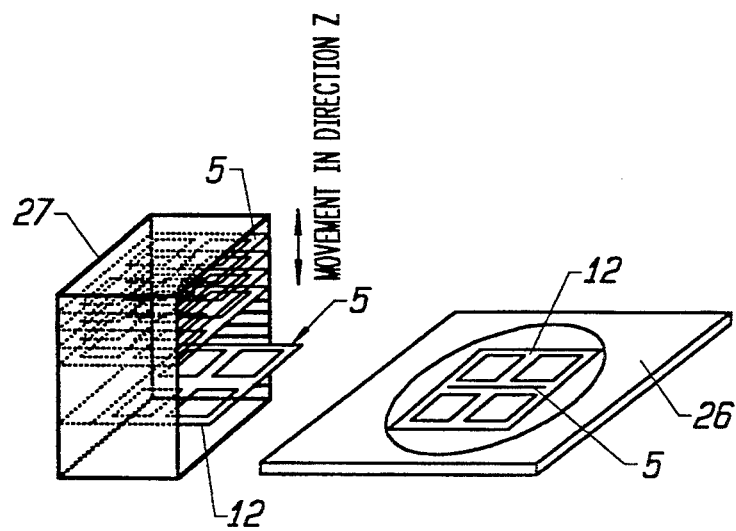
FIG. 7 is a diagram showing retrieval of the active matrix liquid crystal display substrate from substrate storage.
Figure 8:
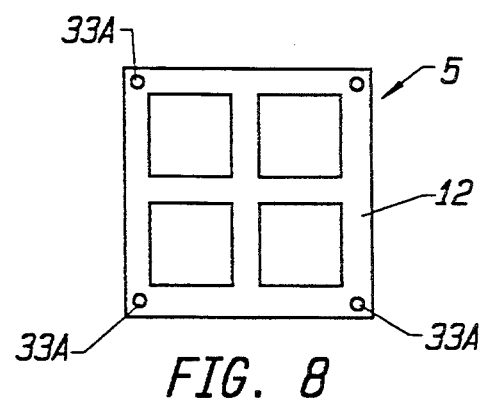
FIG. 8 is a diagram of the active matrix liquid crystal display substrate.

In this example of an active matrix liquid crystal display substrate 5, as shown in FIGS. 7 and 8, a plurality of rectangular areas, comprising source lines 10, gate lines 11, pixel electrodes 13, switching elements 14, shorting bar 15, and shorting bar 16, are formed on one substrate 12.

In step 2 the active matrix liquid crystal display substrates 5 are conveyed to substrate storage part 21 of the testing apparatus and are stored in a cassette. In step 3, the active matrix liquid crystal display substrates 5 stored in substrate storage part 21 are retrieved from substrate storage part 21 and are placed on table 26. In step S4, the active matrix liquid crystal display substrate 5 is affixed to the upper surface of table 26 by vacuum adhesion.

In step S5, table 26 is moved along guide rail 25 (movement in the direction of the X-axis) to the area opposing scanning head 22. In step 6, table 26 is moved in a forward and backward direction for small distances, accurately positioning table 26 beneath scanning head 2.

In step S7, holder 33 provided on scanning head 22 moves downward and electro-optical element 2 is positioned adjacent to active matrix liquid crystal display substrate 5. At this time, the positioning pivots 33a on the outer part of holder 33 are attached (by compression) to fixed positions on active matrix liquid crystal display substrate 5.

Positioning is such that, as shown in FIG. 8, a plurality (in this example 4) of areas are formed on a rectangular substrate 12. Positioning pivots 33a of holder 33 make contact at fixed positions at the four corners of substrate 12, and active matrix liquid crystal display substrate 5 and electro-optical element 2 are aligned in parallel.

In step S8, an electrode of voltage source 7 makes contact with shorting bars 15 and 16 of the active matrix liquid crystal display substrate 5. In step S81, the voltage value is slowly raised so as to become positive with respect to the source side and the gate side, and the current between source lines 10 and gate lines 11 is monitored for leakage. If current leakage is detected, a determination is made that a short (called a cross short) has occurred between source lines 10 and gate lines 11. If there is no leaking current, step S9 is proceeded to. In active matrix liquid crystal display substrate 5 in which a cross short has been detected, in step S81 it is determined whether the active matrix liquid crystal display substrate will be repaired by a repair apparatus or be rejected and disposed of.

In step S9, a bias voltage is applied between the electrode on the upper surface of the electro-optical element and the gate side and the source side in step 8. This bias voltage is a voltage of maximally +15 V with respect to a standard voltage (for example, a grounding level) and is applied in an appropriate mode, and defect testing is thus conducted. In this manner, an electric field is generated between transparent thin film electrodes 2a on the upper surface of the electro-optical element and the pixel electrodes on active matrix liquid crystal display substrate 5.

Figure 10:
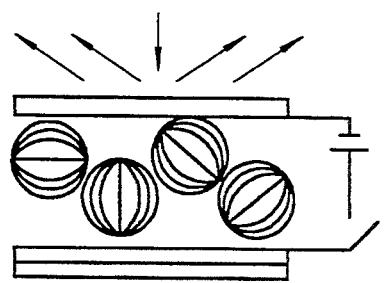
FIG. 10 is a cross sectional diagram of the liquid crystal sheet across which an electric field is not being impressed.
Figure 11:
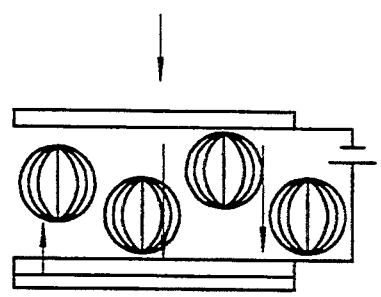
FIG. 11 is a cross sectional diagram showing the liquid crystal sheet across which an electric field is being impressed.

When a liquid crystal sheet 8 is used as electro-optical element 2, when an electric field is not being applied, as shown in FIG. 10, the (ball form) liquid crystal molecules face in disordered directions, scatter the light, and do not permit the transmission of light. When an electric field is impressed as shown in FIG. 11, the liquid crystal molecules (in ball form) all face in a single direction and permit the transmission of light. There is an area in which the transparent electrodes change in linear proportion to voltage changes with respect to the polymer-dispersed liquid crystals. Using this linearity, it is possible to determine the change in voltage as a change in the amount of light transmitted. A bias voltage is applied between pixel electrodes 13 and transparent thin film electrodes 2a on electro-optical element 2 correspond to this linear region.

If a liquid crystal sheet 8 is used, by applying a voltage between the pixel electrodes 13 and the transparent thin film electrodes 2a of electro-optical element 2, an electric field is generated, and electro-optical element 2 has an amount of light transmitted which changes in response to changes in the electric field generated by each pixel electrode 13.

In step S9, light is irradiated from light source 1 onto electro-optical element 2. This light passes through electro-optical element 2 and is reflected by light reflecting body 9. The strength of the light which again passes through electro-optical element 2 is measured by light detector 3.

In step S10, the light received by light detector 3 is calculated in controller 40, and a corresponding voltage is calculated. Provided the value of this corresponding voltage can be specified, the corresponding voltage generated by each pixel is checked based on a threshold value which is determined. In step S11, based on the brightness of the picture or the value of the corresponding voltage, a determination judgement is made as to whether the pixels are defective or not. In order to determine whether an active matrix liquid crystal display substrate 5 is to be accepted or not, standards are used. If a value indicating how many defects are allowed, in a liquid crystal display element with 1,000,000 pixels is decided in advance, a user can determine whether an active matrix liquid crystal display substrate 5 is acceptable based on data of the processing screen.

If the number of defects in an active matrix liquid crystal display substrate 5 is within an acceptable range, the active matrix liquid crystal display substrate 5 is conveyed to the next process in step S12.

If the number of defects exceeds the acceptable limit, repairable units are sent to a repair station in step S13, or in step S14 are sent to a cutting apparatus, or a deposit apparatus and repaired. After repair, it is possible to return the units to the manufacturing line in step S12.

Units which have been determined to be difficult to repair in step S11 are rejected and disposed of in step S15.

Various types of defects can occur in the active matrix liquid crystal display substrates 5 which are detected in step S9. Various test conditions are possible, and can combine to detect numerous types of defects.

The voltage applied with respect to the gate and source lines is 0 v. in the initial condition.

Figure 12:
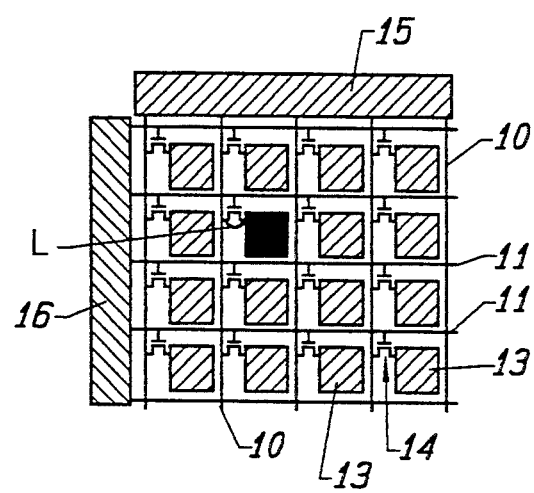
FIGS. 12-17 are expanded views to aid in explaining defective parts in the active matrix liquid crystal display substrate.

As shown by reference L in FIG. 12, when a short circuit defect exists between the source and the drain, by applying a positive voltage on the source lines alone, pixel electrode 13 becomes bright at the pixel shown by the blackened area of FIG. 12, while the other normal pixel electrodes 13 of the pixels do not exhibit any effect, as shown by the slanted lines.

Figure 13:
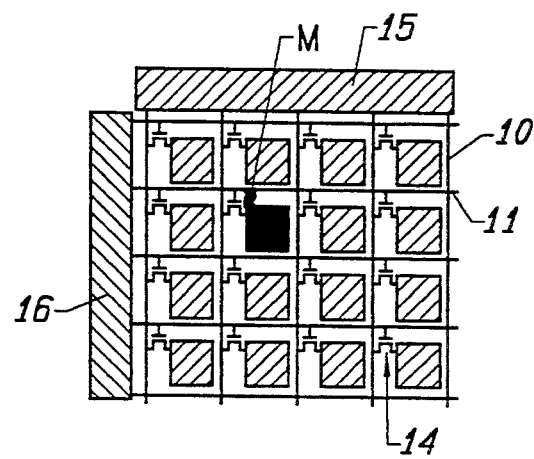

To detect a short circuit, as shown by reference M, between the gate line and the drain lines as shown in FIG. 13, a positive voltage is applied on the gate line and one pixel electrode 13 becomes bright as shown by the blackened section of FIG. 13, while the other pixel electrodes 13 of normal pixels do not change, as shown by the slanted lines.

Figure 14:
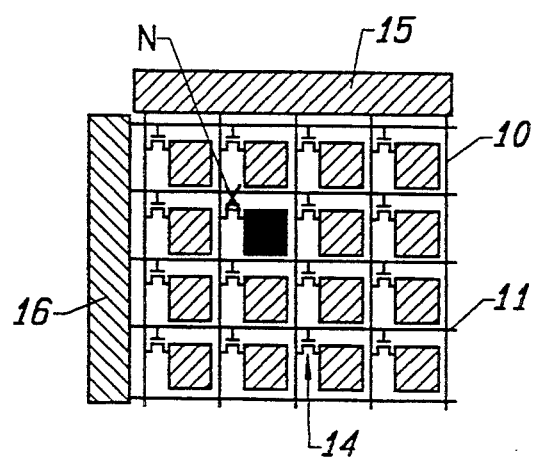

As shown in FIG. 14, when a transistor gate comprising a switching element is disconnected, as shown by reference N, by applying a positive voltage on the source lines and gate lines, 1 pixel electrode 13 does not change, as shown by the blackened part 3 in FIG. 14, while the other normal pixel electrodes 13 become bright, as shown by the slanted lines.

Figure 15:
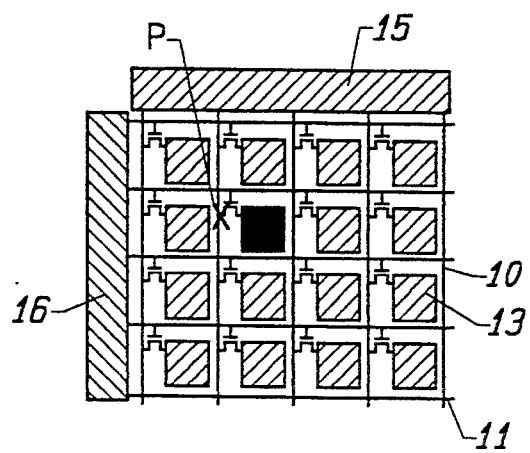

As shown in FIG. 15, when a transistor source comprising a switching element 14 is disconnected, as shown by reference P, by applying a positive voltage on the source lines and the gate line, one pixel electrode 13 does not change, as shown by the blackened part in FIG. 15, while the other, normal pixel electrodes 13 become bright as shown by the slanted lines.

Figure 16:
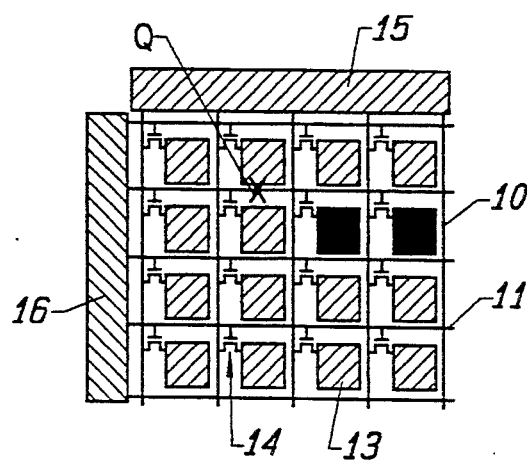

As shown in FIG. 16, when gate lines 11 are open-circuit, as shown by reference Q, by applying a positive voltage on the source lines and the gate lines, a row of pixel electrodes 13 past the open circuit, shown on the right side of the disconnected part, do not change, as shown by the blackened part in FIG. 16, while the other pixel electrodes 13 with normal pixels become bright as shown by the slanted lines.

Figure 17:
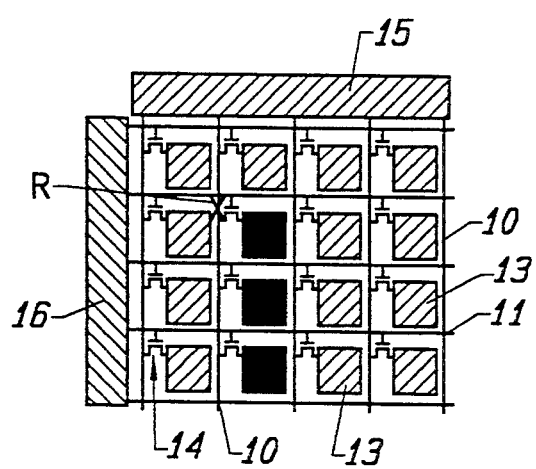

As shown in FIG. 17, when a source line 10 has an open circuit, as shown by reference R, by applying a positive voltage on the source lines and the gate lines, a row of pixel electrodes 13 located past the disconnected part do not change, as shown by the blackened parts in FIG. 17, while the other, normal pixel electrodes 13 turn bright as shown by the slanted lines.

In the above diagrams, the brightness of the pixel electrodes 13 of the active matrix liquid crystal display substrate 5 were shown for ease of understanding. In reality, the parts of the electro-optical element 2 corresponding to pixel electrodes 13 are observed as a brightness distribution. By referring this brightness to a one-pixel dimensional pitch in controller 40, a technique for discriminating the brightness of the pixel elements is obtained.

In the above examples, a positive voltage was applied. Defects can be detected by applying a negative voltage as well, as explained below.

The voltage applied on the gate and source lines is 0 v., as the initial condition.

As shown by reference L in FIG. 12, when a short circuit defect exists between the source and the gate, by applying a negative voltage on the source lines alone, pixel electrode 13 becomes dark at the location shown by the blackened part in FIG. 12, while the other, normal pixel electrodes 13 do not exhibit any effect as shown by the slanted lines.

To detect a defect causing a short circuit, as shown by reference M, between the gate line and the drain lines as shown in FIG. 13, by applying a negative voltage on the gate line from the initial condition, one pixel electrode 13 becomes dark at a location shown by the blackened part in FIG. 13, while the other, normal pixel electrodes 13 do not change as shown by the slanted lines.

As shown in FIG. 14, when a transistor gate comprising a switching element is disconnected as shown by reference N, by applying a positive voltage on the gate lines and a negative voltage on the source lines, one pixel electrode does not change as shown by the blackened part 3 in FIG. 14 while the other, normal pixel electrodes 13 become dark as shown by the slanting lines.

As shown in FIG. 15, when the transistor source comprising a switching element 14 is disconnected as shown by reference P, by applying a positive voltage on the gate lines and a negative voltage on the source lines, one pixel electrode 13 does not change, as shown by the blackened part in FIG. 15, while the other, normal pixel electrodes become dark as shown by the slanted lines.

As shown in FIG. 16, when gate lines 11 are disconnected, as shown by reference Q, by applying a positive voltage on the gate lines and a negative voltage on the source lines, a row of pixel electrodes 13 located past the open circuit, shown on the right side of the disconnected part do not change, as shown by the blackened part in FIG. 16, while the other, normal pixel electrodes 13 become dark as shown by the slanted lines.

As shown in FIG. 17, where source line 10 is disconnected, as shown by reference R, by applying a positive voltage on the gate lines and a negative voltage on the source lines, a row of pixel electrodes 13 located past the disconnected part do not change as shown by the blackened parts in FIG. 17, while the other, normal pixel electrodes 13 become bright as shown by the slanted lines.

By observing the voltage distribution corresponding to each pixel, and on changes in the number and position at which the changes occur, it is possible to determine the number and position of defective parts in an active matrix liquid crystal display substrate 5.

Figure 18A:
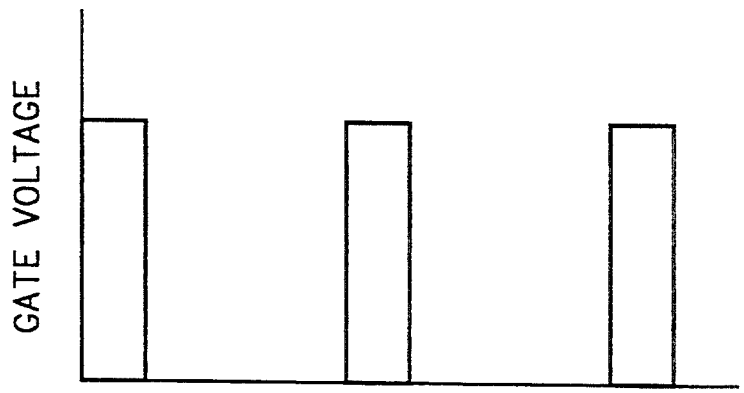
FIGS. 18a, 18b, 19a, 19b, 20a and 20b are graphs to aid in explaining examples of the voltage which is applied during testing.
Figure 18B:
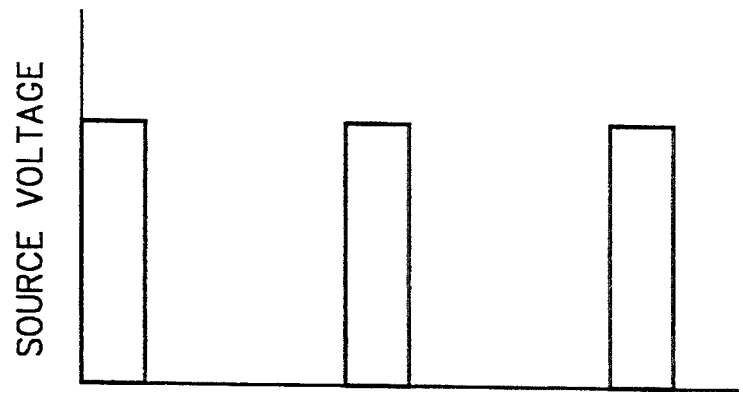

It is possible to detect defects by applying a constant, fixed voltage. However, it is also possible to conduct testing by applying a voltage pulse. For example, it is possible to discriminate the flawed points occurring as a result of short circuits as shown in FIGS. 12 and 13 from normal pixels by applying a voltage pulse as shown in FIGS. 18(a) and (b). Only the flawed pixels will become bright, or dark, respectively. For open-circuit defects, like those shown in FIG. 14 to FIG. 17, by applying a voltage with a mode such as that shown in FIGS. 18(a) and (b), the normal pixels will become bright, while in the case in which there is a open-circuit defect, a line or point which does not change will appear.

Figure 19A:
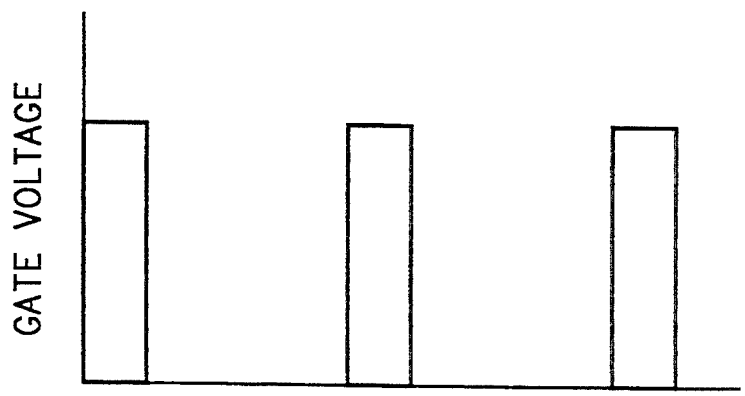
Figure 19B:
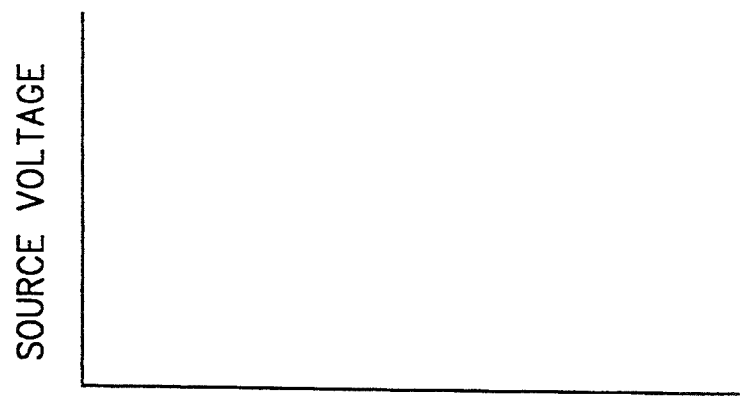

In order to discriminate source-drain short circuits from gate-drain short circuits, it is advantageous to apply a voltage such as that shown in FIGS. 19(a) and (b). Only pixels which are defective as a result of short circuits between the source and the drain will become bright or dark, respectively.

Figure 20A:
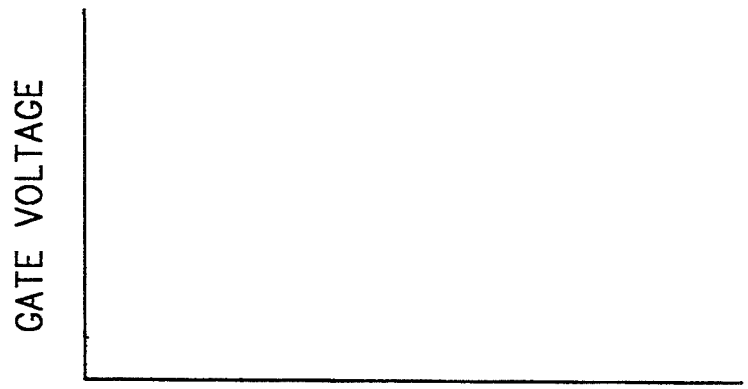
Figure 20B:
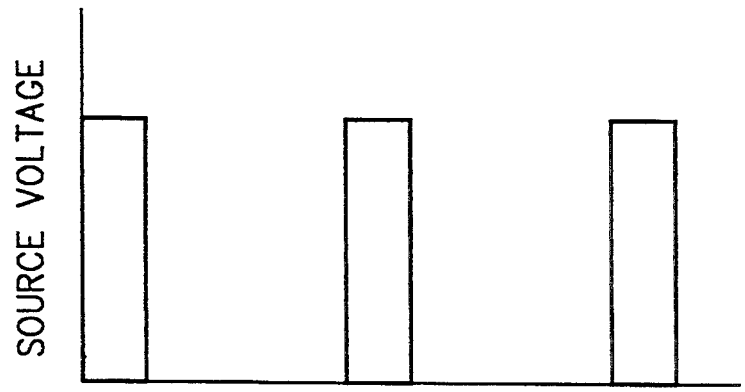

For gate-drain short circuit defects alone, it is advantageous to apply a voltage such as that shown in FIGS. 20(a) and (b). Only short circuit defects between the gate and the drain will become bright or dark, respectively.

When the resistance of these short circuits is high, even if a voltage pulse is applied, these parts may appear normal. However, by applying a sufficiently long pulse, these defects can be detected. By combining the times at which the voltage pulses are applied to both the gate and the source lines of FIGS. 18(a) and (b), it is possible to determine the resistance of the short circuit. By appropriately modulating the voltage pulse, pulse width and period, as shown in FIGS. 18(a) and (b), and by detecting the attenuation time constants of the brightness of the pixels, it is possible to make such a determination.

The present invention recreates a test which is close to the conventional final test before forming active matrix liquid crystal display substrates 5 into liquid crystal panels. The present invention is capable of detecting defects prior to completing the manufacture of liquid crystal panels relatively easily, and is useful in increasing the rate of acceptable products in line.

When the testing method of the present invention is employed, it is possible to test for short-circuited electrodes, as shown in FIGS. 12–17. It is possible to move the substrates in a fashion in which protection from static electricity is maintained, especially for processes in which static electricity is more likely to be generated, such as assembly of liquid crystal panels, or the like. Various configurations, including units which have an IC driver mounted in place of a short circuit electrode, or units which have a drive circuit mounted, or substrates having a drive circuit, or substrates having no short circuit electrode, can also be tested. The present invention may be used on any substrate configuration.

The electro-optical element can be used without any restriction based on the dimensions of the pixel electrodes on the active matrix liquid crystal display substrate (which is the object of testing) such that it has a broad range of applications, is highly reliable, and the costs thereof are relatively low.

Light reflected from the electro-optical element 2 is converted to a corresponding voltage and defects are determined based on this corresponding voltage, so that it is possible to quickly conduct tests in a short time. For example, the inventors conducted tests on a 10-inch active matrix liquid crystal display substrate using a liquid crystal sheet as the electro-optical element and a test apparatus which was actually constructed such that the resolution of the liquid crystal sheet was 50 μm. It was possible to conduct testing, including handling (including the machine controlled speed) of active matrix liquid crystal display substrates 5 at a rate of more than 12 per hour.

By increasing the number of light detectors 3 (CCD camera), a plurality of active matrix liquid crystal display substrates 5 could be tested at one time, and an increase in the number of units processed would be achieved.

As explained above, in the present invention, an electro-optical element is disposed over an active matrix liquid crystal display substrate which is to be tested. An electric voltage is then applied between the pixel electrodes on the active matrix liquid crystal display substrate and the transparent thin film electrodes on the upper surface of the electro-optical element. The optical properties of the electro-optical element cause a change in the light which is transmitted through the electro-optical element. These changes are detected by a light detector. The detection of defects in an active matrix liquid crystal display substrate is thus carried out, so that by monitoring the output of the light detector, defects in the active matrix liquid crystal display substrate can be detected as a group electrically, and reliable and rapid testing can be accomplished.

When a polymer-dispersed liquid crystal is used as the electro-optical element, it is possible to detect defects based on the transmission rate of light through the polymer-dispersed liquid crystal. When a Pockels crystal plate is used, it is possible to detect defects based on the change in the amount of polarization of the reflected light. When polymer-dispersed liquid crystals are used, it has been observed that the test system responds better to red light, and the relationship between the change in voltage of the polymer-dispersed liquid crystal and the transmission ratio is close to a linear relationship, making it is possible to conduct highly accurate testing.

I claim:

1. A method for testing active matrix liquid crystal display substrates having thin film transistors, a plurality of pixel electrodes, a plurality of source lines, and a plurality of gate lines formed on a substrate, comprising the steps of:

employing an active matrix liquid crystal display substrates to be tested; employing an electro-optical element, in which the optical properties change when an electrical field is applied thereon;

placing said electro-optical element immediately above said active matrix liquid crystal display substrate, and separated therefrom by an extremely small gap;

applying an electric voltage between pixel electrodes on said active matrix liquid crystal display substrate and a transparent thin film electrode on the surface of said electro-optical element, thus creating an electrical field across the electro-optical element;

detecting local changes in the optical properties of the electro-optical element, thereby detecting defects in the pixels of an active matrix liquid crystal display substrate.

2. A method for testing active matrix liquid crystal display substrates as stated in claim 1 in which defects in the pixels are detected based on changes in the light transmission rate of polymer-dispersed liquid crystals.

3. A method for testing active matrix liquid crystal display substrates as stated in claim 1 in which Pockels crystals are used as said electro-optical element, and detecting defects in the pixels is based on detecting changes in the amount of polarization of the light reflected from the Pockels crystals.

4. A method for testing active matrix liquid crystal display substrates as stated in claim 1 and having the following additional steps:

irradiating the electro-optical element with light;
   receiving the light reflected from the electro-optical element in a light detector;
   converting the amount of change in the reflected light received by the light detector to a corresponding voltage, and thus discerning the presence of defects in the pixels.

5. The method of claim 1 wherein said plurality of source lines are shorted together, and said plurality of gate lines are shorted together.

6. The method of claim 1 wherein said electric current exists by a voltage applied between said transparent thin film electrodes and said pixel electrodes.

7. A method of testing active matrix liquid crystal display panels comprising:

providing a partially completed active matrix liquid crystal display panel, said panel comprising a plurality of pixel electrodes, a plurality of source lines, and a plurality of gate lines;

shorting said plurality of source lines, and shorting said plurality of gate lines;

placing a voltage difference between said shorted plurality of source lines and said shorted plurality of gate lines;

monitoring said voltage difference using a current detection means for determining a leakage current between said source lines and said gate lines, and removing said panel when said leakage current is detected;

positioning said panel adjacent to a thin film electrode of an electro-optical element with a small gap therebetween, said electro-optical element including optical properties that change when an electric field is impressed thereon;

placing an electric field between said thin film electrode of said electro-optical element and said plurality of pixel electrodes; and locating defects in said plurality of pixel electrodes by examining said electro-optical element optical properties.

* * * * *